(12) United States Patent
Zhang et al.

(10) Patent No.: US 10,794,923 B2
(45) Date of Patent: Oct. 6, 2020

(54) WIPING-TYPE SAMPLE SAMPLING AND FEEDING DEVICE, CARD READING APPARATUS, AND GATE MACHINE APPARATUS

(71) Applicants: NUCTECH COMPANY LIMITED, Beijing (CN); Tsinghua University, Beijing (CN)

(72) Inventors: Qingjun Zhang, Beijing (CN); Yuanjing Li, Beijing (CN); Ziran Zhao, Beijing (CN); Qiufeng Ma, Beijing (CN); Ge Li, Beijing (CN); Biao Cao, Beijing (CN); Qi Mao, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 246 days.

(21) Appl. No.: 15/868,878

(22) Filed: Jan. 11, 2018

(65) Prior Publication Data

US 2018/0196078 A1   Jul. 12, 2018

(30) Foreign Application Priority Data

Jan. 11, 2017 (CN) .......................... 2017 1 0020543

(51) Int. Cl.
*G01N 35/04* (2006.01)
*G01N 1/02* (2006.01)
(Continued)

(52) U.S. Cl.
CPC ............... *G01N 35/04* (2013.01); *G01N 1/02* (2013.01); *G01N 35/00584* (2013.01);
(Continued)

(58) Field of Classification Search
CPC .......... H01J 49/004; H01J 49/00; H01J 49/04; G01N 35/04; G01N 35/00584; G01N 1/02;
(Continued)

(56) References Cited

U.S. PATENT DOCUMENTS 2,578,354 A * 12/1951 Henning .................. B29C 48/06
425/71
2004/0195499 A1* 10/2004 Ishikawa .............. G01N 1/2214
250/281
(Continued)

FOREIGN PATENT DOCUMENTS

CN   101571458 A   11/2009
CN   102478466 A   5/2012
(Continued)

OTHER PUBLICATIONS

First Office Action issued in connection with Japanese Patent Application No. 2018-002495, dated Dec. 3, 2018.
(Continued)

*Primary Examiner* — Benjamin R Whatley
*Assistant Examiner* — Curtis A Thompson
(74) *Attorney, Agent, or Firm* — Knobbe, Martens, Olson & Bear LLP (57) ABSTRACT

The present invention discloses a wiping-type sample sampling and feeding device, a card reading apparatus, and a gate machine apparatus. The wiping-type sample sampling and feeding device comprises a thermally desorbing portion for analyzing a substance; a wiping-type sampling portion for wiping the substance on a card or certificate and includes a first wheel, a second wheel and a wiping conveyor belt that travels between the first and second wheels along a first direction; and a card/certificate conveyor portion including a card carrying belt configured to convey a card or certificate
(Continued)

along a second direction so that the card or certificate can contact with the wiping conveyor belt during conveyance of the card or certificate, thereby the wiping conveyor belt wipes a surface of the card or certificate, wherein the second direction is substantially perpendicular to the first direction.

11 Claims, 3 Drawing Sheets

(51) Int. Cl.
    *G01N 35/00*     (2006.01)
    *G01N 1/00*     (2006.01)
    *G01N 27/62*     (2006.01)
    *G01N 1/22*     (2006.01)
    *H01J 49/04*     (2006.01)
    *H01J 49/00*     (2006.01)
    *G01N 33/15*     (2006.01)
    *G01N 1/24*     (2006.01)
    *G01N 33/22*     (2006.01)

(52) U.S. Cl.
    CPC ............... *G01N 1/00* (2013.01); *G01N 1/22* (2013.01); *G01N 1/2214* (2013.01); *G01N 1/24* (2013.01); *G01N 27/62* (2013.01); *G01N 33/15* (2013.01); *G01N 33/22* (2013.01); *G01N 2001/022* (2013.01); *G01N 2001/024* (2013.01); *G01N 2001/028* (2013.01); *G01N 2035/00346* (2013.01); *H01J 49/00* (2013.01); *H01J 49/004* (2013.01); *H01J 49/04* (2013.01)

(58) Field of Classification Search
    CPC .......... G01N 33/22; G01N 1/24; G01N 33/15; G01N 1/22; G01N 1/2214; G01N 27/62; G01N 1/00; G01N 2001/024; G01N 2001/028; G01N 2035/00346; G01N 2001/022; G01N 35/00
    See application file for complete search history.

(56) References Cited

U.S. PATENT DOCUMENTS

| | | | |
|---|---|---|---|
| 2004/0227938 | A1 | 11/2004 | Craig |
| 2007/0086925 | A1* | 4/2007 | O'Donnell ........... G01N 1/2214 422/82.05 |
| 2008/0217524 | A1* | 9/2008 | Mawer .................. G01N 1/02 250/281 |
| 2008/0264186 | A1* | 10/2008 | Nacson .................. G01N 1/02 73/863.12 |
| 2010/0276589 | A1* | 11/2010 | McKay ............... H01J 49/0431 250/288 |
| 2014/0345364 | A1* | 11/2014 | Lin ...................... G01N 27/622 73/28.01 |

FOREIGN PATENT DOCUMENTS

| | | |
|---|---|---|
| CN | 103245526 A | 8/2013 |
| CN | 105738543 A | 7/2016 |
| CN | 206515350 U | 9/2017 |
| EP | 2 793 014 A1 | 10/2014 |
| JP | 3005433 U3 | 12/1994 |
| JP | H09-038550 A | 2/1997 |
| JP | 2011-237453 A | 11/2011 |
| WO | WO 91/09307 A1 | 6/1991 |
| WO | WO 2007/089221 A2 | 8/2007 |

OTHER PUBLICATIONS

Extended European Search Report dated Jun. 6, 2018, received in connection with European Patent Application No. 18151182.5.

* cited by examiner

WIPING-TYPE SAMPLE SAMPLING AND FEEDING DEVICE, CARD READING APPARATUS, AND GATE MACHINE APPARATUS

CROSS-REFERENCE TO RELATED APPLICATION

The present application claims priority to Chinese Patent Application No. 201710020543.3, filed on Jan. 11, 2017, entitled "WIPING SAMPLING AND FEEDING DEVICE, CARD READING APPARATUS, AND GATE MACHINE APPARATUS", which is incorporated herein by reference in its entirety.

BACKGROUND OF THE INVENTION

Technical Field

The present invention relates to the technical field of security inspection, and particularly to a wiping sampling and feeding device, a card reading apparatus, and a gate machine apparatus.

Background Art

In order to prevent terrorist activities and drug smuggling, various techniques for inspection of trace drugs and explosives have currently been developed. In order to cooperate with the inspection, it needs to provide an efficient and quick sampling device for inspection of cards or certificates.

SUMMARY OF THE INVENTION

According to an aspect of the present application, it provides a wiping sampling and feeding device, comprising:

a thermally desorbing portion configured to thermally desorb a sample fed into the thermally desorbing portion;

a wiping sampling portion including a first wheel and a second wheel that are rotatable about their respective axes, and a wiping conveyor belt that is tensioned by the first and second wheels and travels between the first and second wheels along a first direction by means of rotation of the first and second wheels, wherein the wiping conveyor belt travels through the thermally desorbing portion to enable the thermally desorbing portion to desorb the sample on the wiping conveyor belt as the wiping conveyor belt enters the thermally desorbing portion; and a card/certificate conveyor portion including a card carrying belt configured to convey a card or certificate along a second direction so that the card or certificate is able to contact and wipe a surface of the wiping conveyor belt during conveyance of the card or certificate, wherein the second direction is substantially perpendicular to the first direction.

In an embodiment, the card carrying belt is provided with at least one card blocker, which is/are spaced apart from one another, for blocking the card or certificate from moving along a third direction opposite to the second direction during conveyance of the card or certificate in a second direction.

In an embodiment, the card carrying belt is provided with at least one card/certificate slot having predetermined depth and shape disposed within the card carrying belt so as to enable a card or certificate to be placed in one of the at least one card/certificate slot so that a surface on one side of the card or certificate is enabled to be wiped by the wiping conveyor belt during conveyance by the card carrying belt, and a side wall of said one of the at least one card/certificate slot is capable of, as the card blocker, blocking the card or certificate from moving along the third direction.

In an embodiment, the at least one card blocker is at least one protrusion that, as the card blocker, is capable of blocking the card or certificate from moving along the third direction while enables a surface of one side of the card or certificate to be wiped by the wiping conveyor belt during conveyance of the card or certificate by the card carrying belt.

In an embodiment, the wiping sampling portion and the thermally desorbing portion are both arranged within a working chamber located above the card carrying belt, and the working chamber is provided with a wiping opening oriented toward an upper surface of the card carrying belt so that the wiping conveyor belt is able to contact a surface of the card or certificate placed on the card carrying belt so as to wipe the surface of the card or certificate; and the working chamber includes a wiping opening seal configured around the wiping opening to contact the card carrying belt when the wiping opening gets close to the card carrying belt so as to prevent external substances from entering the wiping opening.

In an embodiment, the wiping sampling portion and the thermally desorbing portion are both arranged within a working chamber located below the card carrying belt, and the working chamber is provided with a wiping opening oriented toward a lower surface of the card carrying belt; and the card carrying belt includes a plurality of card carrying belt wiping openings correspondingly provided at locations adjacent to the card blocker, wherein the card carrying belt wiping opening is configured to enable the wiping conveyor belt to contact with the card or certificate placed on the card carrying belt through the card carrying belt wiping opening when the card or certificate is on the card carrying belt, thereby wiping a lower surface of the card or certificate;

the working chamber includes a wiping opening seal configured around the wiping opening to contact the card carrying belt when the wiping opening gets close to the card carrying belt so as to prevent an outward leakage of a wiped sample, and maintain gas tightness of the working chamber in order to intake carrier gas under a pressure so as to realize entry of the sample to a downstream component.

In an embodiment, the thermally desorbing portion includes a thermally desorbing chamber that comprises a wiping conveyor belt entrance for entry of the wiping conveyor belt to the thermally desorbing chamber, a wiping conveyor belt exit for exit of the wiping conveyor belt from the thermally desorbing chamber, and a sample outlet for export of the sample from the thermally desorbing chamber.

In an embodiment, the thermally desorbing chamber includes a wiping conveyor belt exit sealing material provided at the wiping conveyor belt exit to seal the wiping conveyor belt exit, maintain gas tightness of the thermally desorbing chamber, and clean the wiping conveyor belt passed through the wiping conveyor belt exit; seal of the wiping conveyor belt exit enables maintenance of gas tightness of the working chamber in order to intake carrier gas under a pressure so as to take the desorbed sample to a downstream component.

In an embodiment, the wiping conveyor belt exit sealing material is a corrugated soft sheath.

In an embodiment, the working chamber allows the wiping sampling portion and the thermally desorbing portion to be accommodated in the working chamber and isolated from external environment, and the wiping sampling and feeding device comprises a gas filtering device within the working chamber for filtering and cleaning the gas in the working chamber.

In an embodiment, the thermally desorbing portion includes a temperature controller for controlling an inner temperature of the thermally desorbing portion at desired temperature, the temperature controller includes a heater provided in the thermally desorbing chamber, a temperature sensor for measuring temperature, and a thermal insulation layer for insulating heat in the thermally desorbing chamber.

Another aspect of the present invention provides a card reading apparatus for reading information of a card or certificate, wherein the card reading apparatus comprises the wiping sampling and feeding device according to above. The card reading apparatus is configured to read the information of the card or certificate when the card or certificate is placed on and conveyed by a card carrying belt, while or after the wiping sampling and feeding device wipes the card or certificate to obtain a sample from a surface of the card or certificate.

Another aspect of the present application provides a gate machine apparatus comprising the card reading apparatus as mentioned above.

BRIEF DESCRIPTION OF THE DRAWINGS

The following description of the figures of specific embodiments of the present invention described herein is merely exemplary in nature and is not intended to limit the scope of the present invention regarding teachings, their application, uses, etc.

DETAILED DESCRIPTION OF THE PREFERRED EMBODIMENT

Although various modifications and alternatives are allowable to the present invention, their specific embodiments are shown in the drawings by the way of examples, and herein will be described in detail. It should be understood that, however, the accompanied drawings and detailed description are not intended to limit the present invention to those specific forms as disclosed, but to cover all of the modifications, equivalents and alternatives within the spirit and range of the present invention defined by the claims as attached. The drawings are for the purpose of illustration, so they may be drawn without proportion. Terms such as 'first', 'second' and 'third' used in the present disclosure are merely to distinguish different components, rather than indicating meanings of significance, sequence, etc.

Hereinafter, embodiments of the present invention will be described with reference to the drawings.

A wiping sampling and feeding device includes a thermally desorbing portion 30 configured to desorb a sample fed into the thermally desorbing portion 30; a wiping sampling portion 40 including a first wheel 13 and a second wheel 14 that are rotatable about their respective axes, and a wiping conveyor belt 15 that is tensioned by the first and second wheels 13, 14 and driven to travel between the first and second wheels 13, 14 along a first direction by means of rotation of the first and second wheels, wherein the wiping conveyor belt 15 moves through the thermally desorbing portion 30 to enable the thermally desorbing portion 30 to desorb the sample on the wiping conveyor belt 15 as the wiping conveyor belt 15 enters the thermally desorbing portion 30; and a card/certificate conveyor portion 50 including a card carrying belt 5 configured to convey a card or certificate 8 along a second direction so that the card or certificate 8 is able to contact the wiping conveyor belt 15 during conveyance of the card or certificate 8, such that the wiping conveyor belt 15 wipes a surface of the card or certificate 8, wherein the second direction is substantially perpendicular to the first direction. The card carrying belt 5 may be made of materials, such as silicon/fluorine rubber, which are elastic and nonvolatile at high temperature.

Figure 1:
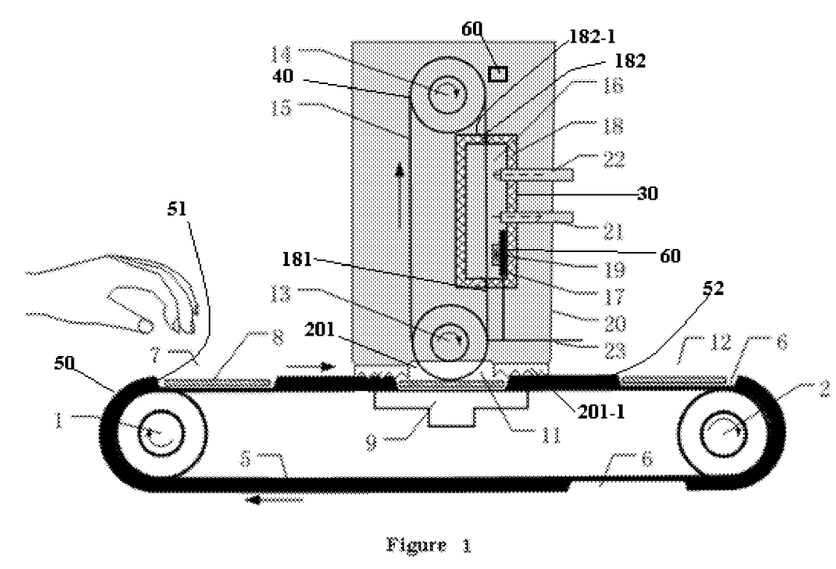
FIG. 1 is a schematic diagram of a wiping sampling and feeding device of an embodiment of the present application.

The card/certificate conveyor portion 50 may include two wheels, e.g., include the wheels 1 and 2 as shown in FIG. 1. The wheels 1 and 2 tension the card carrying belt 5 so that the card carrying belt 5 may provide sufficient support when the card or certificate 8 is wiped. The wheels 1 and 2 rotate simultaneously, thereby driving the card carrying belt 5 to convey clockwise. It is should be understood that the card carrying belt 5 may convey counterclockwise.

In the embodiment shown in FIG. 1, the first direction is a vertical direction, while the second direction is a horizontal direction, and in particular the second direction is a rightward horizontal direction.

In the embodiment shown in FIG. 1, the card carrying belt 5 is provided with at least one card blocker 51, which is/are spaced apart from one another, for blocking the card or certificate 8 during conveyance of the card or certificate 8 in a second direction from moving along a third direction opposite to the second direction. The third direction is a leftward horizontal direction.

Figure 2:
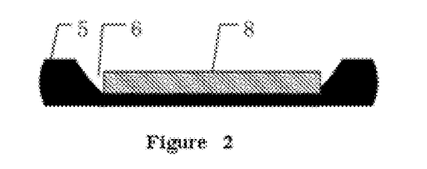
FIG. 2 is a cross-sectional schematic diagram of a card carrying belt of a wiping sampling and feeding device of an embodiment of the present application.
Figure 3:
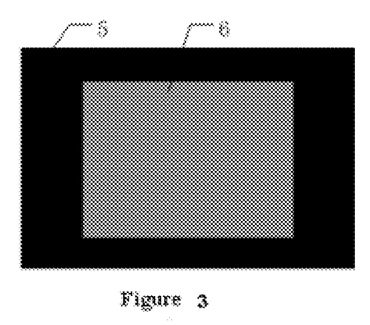
FIG. 3 is a schematic top view of a card carrying belt of a wiping sampling and feeding device of an embodiment of the present application.

In an embodiment, the card carrying belt 5 is provided with at least one card/certificate slot 6 having predetermined depth and shape, which is disposed within the card carrying belt 5, so as to enable a card or certificate 8 to be placed in one of the at least one card/certificate slot 6 so that a surface on one side of the card or certificate 8 can be wiped by the wiping conveyor belt 15 during conveyance of the card or certificate 8 by the card carrying belt 5. In the embodiment, a side wall of said one of the at least one card/certificate slot, as the card blocker 51, can block the card or certificate 8 from moving along the third direction. For example, in the embodiment shown in FIG. 1, card/certificate slots 6 are arranged in the card carrying belt 5, and are spaced apart from one another. The card/certificate slot 6 is sized to allow the card or certificate 8 to be placed in the card/certificate slot 6. An upper surface of the card or certificate 8 is aligned with or slightly higher than an upper surface of the card carrying belt 5. FIG. 2 illustrates a cross-sectional view of a card/certificate slot 6, in which an upper surface of the card or certificate 8 is actually lower than an upper surface of the card carrying belt 5. It makes no difference that, with the above configuration, the upper surface of the card or certificate 8 can be wiped by the wiping conveyor belt 15. FIG. 3 is a top view of the card or certificate 8 being placed on the card carrying belt 5. As the card carrying belt 5 moves along the direction indicated by the arrow in FIG. 1, firstly, the card or certificate 8 is placed in a card/certificate slot 6 in the left side of the card carrying belt 5, while the card carrying belt 5 is conveying the card or certificate 8 toward the right side. Meanwhile, the wiping conveyor belt 15 of the wiping sampling portion 40 moves along the direction indicated by the arrow in FIG. 1. It can be seen that the wiping conveyor belt 15 of the wiping sampling portion 40 contacts the card or certificate 8 on the card carrying belt 5 at a middle location in FIG. 1. The speed of the wiping conveyor belt 15 at the contact point with the card or certificate 8 has a leftward horizontal component, while the speed of the card carrying belt 5 has a rightward horizontal component. Thereby, the wiping conveyor belt 15 wipes an upper surface of the card or certificate. It should be understood that the leftward horizontal component of the speed of the wiping conveyor belt 15 may be set as required. In the embodiment in which the card/certificate slot 6 is provided, in fact, as long as there is difference between the horizontal component of the speed of the wiping conveyor belt 15 and the horizontal component of the speed of the card carrying belt 5, the wiping conveyor belt 15 can wipe the upper surface of the card or certificate 8. According to the embodiment, an effect of wiping will be improved as said difference increases.

It is possible to control the time of wiping the card or certificate 8 and the thermally desorbing time of the substance on the wiping conveyor belt 15 by controlling movements of the card carrying belt 5 and the wiping conveyor belt 15. For example, in an embodiment, assuming that the speed of the card carrying belt 5 is 0.2 m/s, the speed of the wiping conveyor belt 15 is 1 m/s, and a length of the card or certificate 8 is 100 mm, then a wiping speed (relative speed) of the wiping conveyor belt 15 relative to the card or certificate 8 is 1.2 m/s, the time for wiping the card or certificate 8 is 8.3 ms, and the desorbing time for the card or certificate 8 that has been wiped for one time is 10 ms. The desorbing time can be considered to be instantaneous. Thus, it is possible to omit those pre-concentration components that are required by conventional gas phase chromatography, and the thermally desorbing portion 30 can be directly connected to a gas phase chromatographic column, or be firstly connected to a six-way valve sampling portion 40 and then connected to a gas phase chromatographic column or IMS or other detectors (in this case, the requirements on gas tightness can be lowered) to perform analysis of substances. In an embodiment, in which a card or certificate placing region is apart away from a card taking region by a distance of 400 mm, it requires just 2 seconds to complete sampling and conveying a card or certificate 8, then a rate of customs inspection reaches 30 people/min. Therefore, it is possible to realize sampling inspection for the passengers successively without reducing the flow rate of people.

In an embodiment, the at least one card blocker 51 may be at least one protrusion 52, which, as the card blocker 51, can block the card or certificate 8 from moving along the third direction while enables a surface of one side of the card or certificate 8 to be wiped by the wiping conveyor belt 15 during conveyance of the card or certificate 8 by the card carrying belt 5.

The wiping sampling and feeding device of the present invention implements automatic wiping sampling manner, achieves higher sampling efficiency and is more suitable for substances with semi-volatility and particles as compared with a directly intake sampling devices. Thus, it can effectively lower the technical requirements on a lowest detection limit of a detector, improve the detection sensitivity, and is more suitable for the requirements of security inspection on substances such as drugs, explosives carried by passengers.

In an embodiment, the wiping sampling portion 40 and the thermally desorbing portion 30 are both arranged in a working chamber 20 located above the card carrying belt 5, for example, as shown in FIG. 1. The working chamber 20 may be constructed or defined, for example, by a housing formed by metal. The working chamber 20 is provided with a wiping opening 201 oriented toward an upper surface of the card carrying belt 5 so that the card or certificate 8 placed on the card carrying belt can contact the wiping conveyor belt 15, so that the wiping conveyor belt 15 wipes a surface of the card or certificate 8. The working chamber 20 includes a wiping opening seal 201 that is used to prevent an outward leakage of a wiped sample, and is configured around the wiping opening to contact the card carrying belt 5 when the wiping opening 201 gets close to the card carrying belt 5. By providing the wiping opening 201 of the working chamber 20, a substantially closing space can be achieved in the working chamber 20 in order to prevent an outward leakage of a wiped sample, maintain gas tightness of the working chamber in order to intake carrier gas under a pressure to drive the sample to enter a downstream chromatogram apparatus or other analysis equipments. As shown in FIG. 1, two wheels are provided in the working chamber 20, and the wheels tense the wiping conveyor belt 15 and drive the wiping conveyor belt 15 to move. The wiping conveyor belt 15 passes through a thermally desorbing chamber 16. The entire working chamber 20 is located above the card carrying belt 5.

Figure 4:
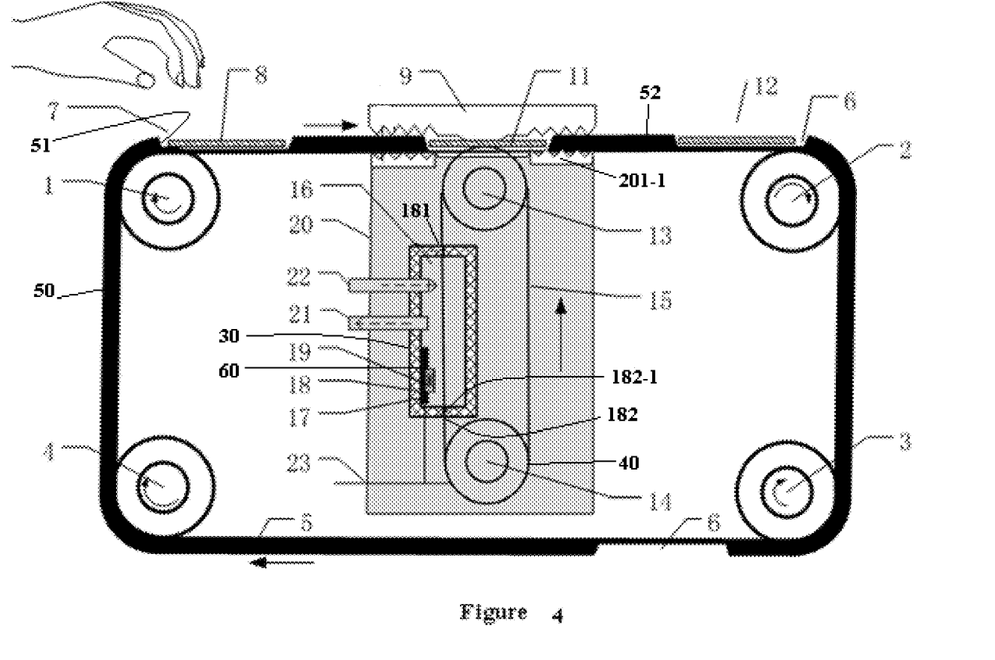
FIG. 4 is a schematic diagram of a wiping sampling and feeding device of another embodiment of the present application.
Figure 5:
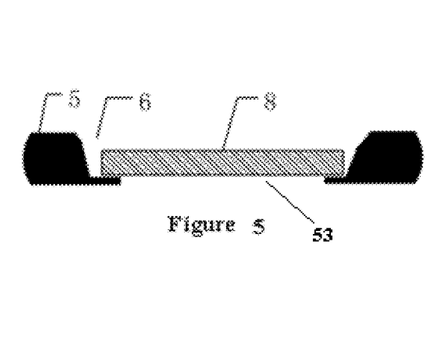
FIG. 5 is a cross-sectional schematic diagram of a card carrying belt of a wiping sampling and feeding device of another embodiment of the present application.
Figure 6:
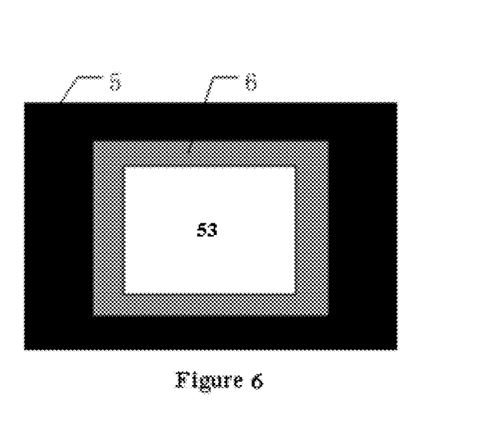
FIG. 6 is a schematic top view of a card carrying belt of a wiping sampling and feeding device of an embodiment of the present application.

In another embodiment, the wiping sampling portion 40 and the thermally desorbing portion 30 are both arranged in a working chamber 20 located below the card carrying belt 5, for example, as shown in FIG. 4. The working chamber 20 is provided with a wiping opening that is oriented toward a lower surface of the card carrying belt 5. In the present embodiment, the card carrying belt 5 includes a plurality of card carrying belt wiping openings correspondingly provided at locations adjacent to the card blocker 51. FIGS. 5 and 6 illustrate a type of card carrying belt 5, in the middle of which a card carrying belt wiping opening is provided, wherein FIG. 5 is a cross-sectional view of a card/certificate slot 6 of the card carrying belt 5, and FIG. 6 is a top view of the card carrying belt 5. The card carrying belt wiping opening is configured to enable the wiping conveyor belt 15 to contact and wipe a lower surface of the card or certificate placed on the card carrying belt 5 through the card carrying belt wiping opening when the card or certificate 8 is on the card carrying belt 5. The size of the card carrying belt wiping opening may be set according to the size of the wiping conveyor belt 15. For example, a width of the wiping conveyor belt 15 may be approximate to a width of the card or certificate, while the card carrying belt wiping opening is smaller than the size of the card or certificate. The working chamber 20 includes a wiping opening seal 201-1 configured around the wiping opening to contact the card carrying belt 5 when the wiping opening gets close to the card carrying belt 5 so as to prevent an outward leakage of a wiped sample and maintain gas tightness of the working chamber 20 to enable intake of carrier gas under a pressure, which facilitates entry of the desorbed sample from a sample exit 21 to a downstream chromatographic column or other analysis equipments connected. It is advantageous that, in the structure as shown in FIG. 4, a pressure pad 9 is provided above the card carrying belt 5. The pressure pad 9 may apply pressure force to the wiping and contact of the card or certificate 8 so as to support the card or certificate 8 to contact the wiping conveyor belt 15. The pressure pad 9 may also assist to seal the working chamber 20. The pressure pad 9 may be made of materials, such as silicon/fluorine rubber, that are elastic and nonvolatile under high temperature. In the embodiment in FIG. 4, it is possible to provide four wheels 1, 2, 3, 4 to tense the wiping conveyor belt 15, and the working chamber 20 may be located in the space surrounded by the four wheels 1, 2, 3, 4. However, such is not always necessary. The structure of the working chamber 20 is similar to that of the working chamber 20 in FIG. 1.

In the structures in FIGS. 1 and 4, the working chamber 20 allows the wiping sampling portion 40 and the thermally desorbing portion 30 to be accommodated in the working chamber 20 and isolated from external environment. The wiping sampling and feeding device may include a gas filtering device 60 within the working chamber 20 configured for filtering and cleaning the gas in the working chamber 20, thereby avoiding leakage of the substance within the working chamber 20 to ambient environment.

In an embodiment, the thermally desorbing portion 30 includes a thermally desorbing chamber 16, which includes a wiping conveyor belt entrance 181 for entry of the wiping conveyor belt 15 to the thermally desorbing chamber 16, a wiping conveyor belt exit 182 for exiting of the wiping conveyor belt 15 from the thermally desorbing chamber 16, and a sample outlet 21 for export of the sample from the thermally desorbing chamber 16. The thermally desorbing chamber 16 includes a wiping conveyor belt exit sealing material 182-1 provided at the wiping conveyor belt exit 182 to seal the wiping conveyor belt exit 182 and clean the wiping conveyor belt 15 passed through the wiping conveyor belt exit 182. The wiping conveyor belt exit sealing material 182-1 may be a corrugated soft sheath. The corrugated soft sheath may be made of materials, such as silicon/fluorine rubber, which are elastic and nonvolatile under high temperature. The thermally desorbing chamber 16 can be provided with a carrier gas inlet 22 for introducing carrier gas into the thermally desorbing chamber 16, and a sample outlet 21 for, through the carrier gas, taking a desorbed sample into downstream analysis components such as a chromatographic column or IMS or MS or other analysis components.

According to the embodiments of the present invention, a closed environment within the working chamber 20 may be achieved, which can be regarded as a first step of sealing; a closing environment within the thermally desorbing portion 30 may be further achieved, which can be regarded as a second step of sealing. Due to the presence of the two steps of sealing, it is possible to form a gas seal with a gas pressure of about 0.01 MPa to 0.06 MPa in the thermally desorbing chamber 16. When a chromatographic column is connected downstream the sample outlet 21, the thermally desorbed sample can generally be taken into a conventional capillary chromatographic column by carrier gas at a gas pressure of about 0.06 MPa, but it can generally only be at a gas pressure of 0.01 MPa in a case where MMC column is used for sample feeding. It is possible to realize sealing of the thermally desorbing chamber 16 by two steps of sealing in order to prevent the sample desorbed by the thermally desorbing chamber 16 from leaking to ambient environment, and ensure that the desorbed sample enter a downstream chromatographic column or other analysis components through the sample exit 21. For example, in the embodiment shown in FIG. 4, the working chamber 20 may be provided with an inlet 23 for electric controlling lines, and a gas filtering device 60 for purifying the gas within the working chamber 20.

The thermally desorbing portion 30 may further include a temperature controller for controlling an inner temperature of the thermally desorbing portion 30 at desired temperature. The temperature controller includes a heater provided in the thermally desorbing chamber 16, a temperature sensor for measuring temperature, and a thermal insulation layer for insulating heat in the thermally desorbing chamber 16. In particular, as shown in FIG. 4, the thermally desorbing chamber 16 includes a heating element 17, a thermal insulation sheath 18 and a temperature sensor 19, which constitute the temperature controller. The thermally desorbing chamber 16 is ensured to be at a desired temperature under the control of a computer so that the sample is desorbed sufficiently. The thermal insulation sheath 18 may be made of aerogel or glass or ceramic wool with a thickness of about 20 mm. The temperature controlling system controls the temperature of the thermally desorbing chamber 16 (between 25° C.~200° C.) to ensure that the sample is desorbed from the wiping conveyor belt 15 and passes through the desorbed sample exit 21 to a downstream component, such as an analysis component, that is connected to the sample exit 21.

Figure 7:
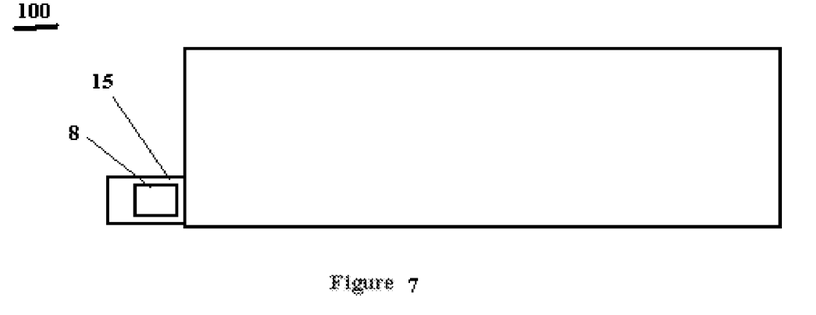
FIG. 7 is a card reading apparatus for reading information of a card or certificate.

An embodiment of the present invention provides a card reading apparatus 100 for reading information of a card or certificate 8, wherein the card reading apparatus 100 includes the above wiping sampling and feeding device. The card reading apparatus 100 is configured to read the information of the card or certificate 8 when the card or certificate 8 is placed on and conveyed by a card carrying belt 5, while or after the wiping sampling and feeding device wipes a surface of the card or certificate 8 to obtain a sample from the surface of the card or certificate 8, thus it is possible to realize combination of reading the information of the inspected person's card/certification with the security inspection of hazardous substances.

Figure 8:
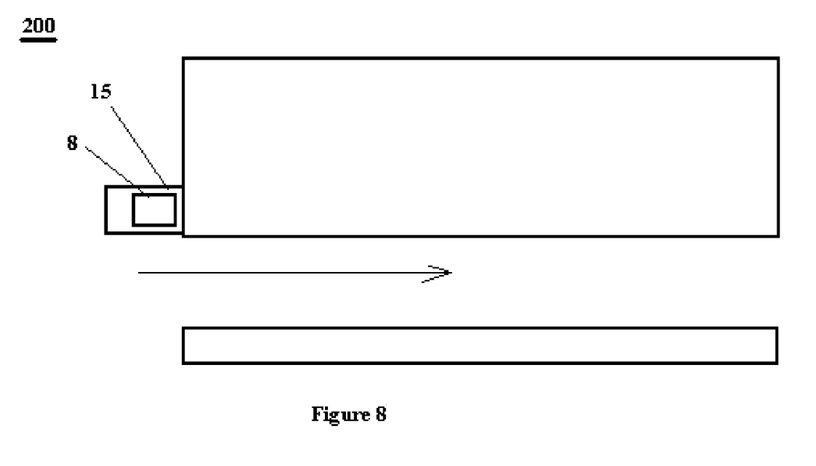
FIG. 8 is a gate machine apparatus including a card reading apparatus for reading information of a card or certificate.

An embodiment of the present invention provides a gate machine apparatus 200 including the card reading apparatus as described above.

The automatic wiping sampling and feeding device of the present disclosure can be equipped to a gate machine apparatus 200, where operating process is as follows. It is possible to control the position of a card/certificate slot 6 according to timing sequence by means of computer-controlled motors and position sensors (now shown). When a passenger arrives an entrance of the gate machine apparatus 200, the card/certificate slot 6 is located just below a card placing region 7. The passenger puts a card or certificate 8 into the card/certificate slot 6 below the card placing region 7, then the card carrying belt 5 is controlled to bring the card or certificate 8 to a wipe region 11. The card or certificate 8 that has entered the wipe region 11 is wiped by a wiping conveyor belt 15 that moves relative to the card or certificate 8. The wiped card or certificate 8 is conveyed to a card reading region 12, and is taken away by the passenger after automatic card reading. Then, card carrying belt 5 enters a next circulation. On the other hand, the wiping conveyor belt 15 that has wiped the card or certificate 8 is brought into a thermally desorbing chamber 16. The wiped sample is desorbed rapidly. The desorbed sample is brought by a sample feeding carrier gas 22, passes through a desorbed sample exit 21, and enters other analysis detection component at downstream. Thus, it is possible to realize sampling inspection on the passengers successively.

The sampling method of the present invention integrates advantages of 'quickness, circulation, full-automation', and can realize quick sampling on the passengers successively. It overcomes the disadvantages of conventional manual sampling that could not achieve high efficiency and that has to conduct selective inspection. It improves the inspection efficiency and is suitable to quick inspections on passengers at the passage sites such as airport/traffic way/railway passes, entrance of conferences, etc. It initiates a new mode for customs inspection of trace substances.

Although some embodiments of the present general invention conception have been illustrated and described, it will be understood by a person skilled in the art that it is possible to make modifications to these embodiments without departing from the and principle and spirit of the present general invention conception. The scope of the present invention is defined by the claims and their equivalents.

What is claimed is:

1. A wiping, sampling and feeding device, comprising:
a thermally desorbing portion configured to thermally desorb a sample fed into the thermally desorbing portion;
a wiping sampling portion including a first wheel and a second wheel that are rotatable about their respective axes, and a wiping conveyor belt that is tensioned by the first and second wheels and travels between the first and second wheels along a first direction by means of rotation of the first and second wheels, wherein the wiping conveyor belt travels through the thermally desorbing portion to enable the thermally desorbing portion to desorb the sample on the wiping conveyor belt as the wiping conveyor belt enters the thermally desorbing portion; and
a card/certificate conveyor portion including a card carrying belt configured to convey a card or certificate along a second direction so that the card or certificate is able to contact and wipe a surface of the wiping conveyor belt during conveyance of the card or certificate, wherein the second direction is substantially perpendicular to the first direction;
wherein the wiping sampling portion and the thermally desorbing portion are both arranged within a working chamber, and the working chamber is provided with a wiping opening oriented toward a surface of the card carrying belt so that the wiping conveyor belt is able to contact a surface of the card or certificate placed on the card carrying belt so as to wipe the surface of the card or certificate,
wherein the card/certificate conveyor portion is not placed in the working chamber,
wherein the card carrying belt includes at least one card/certificate slot having predetermined depth and shape disposed within the card carrying belt so as to enable the card or certificate to be placed in one of the at least one card/certificate slot so that the surface of the card or certificate is enabled to be wiped by the wiping conveyor belt during conveyance by the card carrying belt, and a side wall of said one of the at least one card/certificate slot is capable of, as a card blocker, blocking the card or certificate from moving along a third direction opposite to the second direction during conveyance of the card or certificate in the second direction.

2. The wiping sampling and feeding device according to claim 1, wherein the card blocker is at least one protrusion that, as the card blocker, is capable of blocking the card or certificate from moving along the third direction while enabling the surface of the card or certificate to be wiped by the wiping conveyor belt during conveyance of the card or certificate by the card carrying belt.

3. The wiping sampling and feeding device according to claim 1, wherein the wiping sampling portion and the thermally desorbing portion are both located above the card carrying belt, and the wiping opening is oriented toward an upper surface of the card carrying belt so that the wiping conveyor belt is able to contact the surface of the card or certificate placed on the card carrying belt so as to wipe the surface of the card or certificate; and the working chamber includes a wiping opening seal configured around the wiping opening to contact the card carrying belt when the wiping opening gets close to the card carrying belt so as to prevent external substances from entering the wiping opening.

4. The wiping sampling and feeding device according to claim 1, wherein the wiping sampling portion and the thermally desorbing portion are both located below the card carrying belt, and the wiping opening is oriented toward a lower surface of the card carrying belt; and the card carrying belt includes a plurality of card/certificate slots correspondingly provided at locations adjacent to the card blocker, wherein the card carrying belt wiping opening is configured to enable the wiping conveyor belt to contact with the card or certificate placed on the card carrying belt through the card carrying belt wiping opening when the card or certificate is on the card carrying belt, thereby wiping the lower surface of the card or certificate;
the working chamber includes a wiping opening seal configured around the wiping opening to contact the card carrying belt when the wiping opening gets close to the card carrying belt so as to prevent an outward leakage of a wiped sample, and maintain gas tightness of the working chamber in order to intake carrier gas under a pressure so as to realize entry of the sample downstream.

5. The wiping sampling and feeding device according to claim 1, wherein the thermally desorbing portion includes a thermally desorbing chamber that comprises a wiping conveyor belt entrance for entry of the wiping conveyor belt to the thermally desorbing chamber, a wiping conveyor belt exit for exit of the wiping conveyor belt from the thermally desorbing chamber, and a sample outlet for export of the sample from the thermally desorbing chamber.

6. The wiping sampling and feeding device according to claim 5, wherein the thermally desorbing chamber includes a wiping conveyor belt exit sealing material provided at the wiping conveyor belt exit to clean the wiping conveyor belt passed through the wiping conveyor belt exit and to seal the wiping conveyor belt exit, maintaining gas tightness of the thermally desorbing chamber, such that the working chamber is maintained with gas tightness in order to intake a carrier gas under a pressure so as to take the desorbed sample downstream.

7. The wiping sampling and feeding device according to claim 3, wherein the working chamber allows the wiping sampling portion and the thermally desorbing portion to be accommodated in the working chamber and isolated from external environment, and the wiping sampling and feeding device comprises a gas filtering device within the working chamber for filtering and cleaning a gas in the working chamber.

8. The wiping sampling and feeding device according to claim 4, wherein the working chamber allows the wiping sampling portion and the thermally desorbing portion to be accommodated in the working chamber and isolated from external environment, and the wiping sampling and feeding device comprises a gas filtering device within the working chamber for filtering and cleaning a gas in the working chamber.

9. The wiping sampling and feeding device according to claim 5, wherein the thermally desorbing portion includes a temperature controller for controlling an inner temperature of the thermally desorbing portion at desired temperature, the temperature controller includes a heater provided in the thermally desorbing chamber, a temperature sensor for measuring temperature, and a thermal insulation layer for insulating heat in the thermally desorbing chamber.

10. An apparatus for reading information of a card or certificate, wherein the apparatus comprises the wiping sampling and feeding device according to claim 1, and further comprises a card reading apparatus configured to read information of the card or certificate when the card or certificate is placed on and conveyed by the card carrying belt, while or after the wiping sampling and feeding device wipes the card or certificate to obtain a sample from the surface of the card or certificate.

11. An apparatus for automatic reading of a card or certificate, wherein the apparatus comprises the card reading apparatus of claim 10 and further comprises an entrance of a gate machine.

* * * * *